United States Patent
Wendelborn

[11] Patent Number: 5,181,523
[45] Date of Patent: Jan. 26, 1993

[54] BLOOD SAMPLING DEVICE WITH BLOOD-VIEWING CHAMBER

[76] Inventor: Dieter Wendelborn, Schwinderstrasse 62, 2090 Drage, Fed. Rep. of Germany

[21] Appl. No.: 761,842
[22] PCT Filed: Dec. 19, 1990
[86] PCT No.: PCT/EP90/02243
  § 371 Date: Sep. 13, 1991
  § 102(e) Date: Sep. 13, 1991
[87] PCT Pub. No.: WO91/10397
  PCT Pub. Date: Jul. 25, 1991

[30] Foreign Application Priority Data
Jan. 16, 1990 [DE] Fed. Rep. of Germany ....... 4000968
Oct. 11, 1990 [DE] Fed. Rep. of Germany ....... 4032274

[51] Int. Cl.⁵ .............................................. A61B 5/00
[52] U.S. Cl. .................................. 128/764; 604/168
[58] Field of Search ............. 128/760, 763, 764, 770; 604/168, 187, 240, 264, 272

[56] References Cited

U.S. PATENT DOCUMENTS

| | | | |
|---|---|---|---|
| 3,382,865 | 5/1968 | Worrall | 128/764 |
| 3,931,815 | 1/1976 | Takatsuki | 128/2 F |
| 4,154,229 | 5/1979 | Nugent | 128/764 |
| 4,207,870 | 6/1980 | Eldridge | 128/764 |
| 4,398,544 | 8/1983 | Nugent et al. | 128/763 |
| 4,416,291 | 11/1983 | Kaufman | 128/763 |
| 4,418,703 | 12/1983 | Hoch et al. | 128/763 |
| 4,444,203 | 4/1984 | Engelman | 128/763 |
| 4,682,980 | 7/1987 | Suzuki | 604/168 |
| 4,821,738 | 4/1989 | Iwasaki et al. | 128/765 |

FOREIGN PATENT DOCUMENTS

WO88/02238 4/1988 PCT Int'l Appl. .
1345979 2/1974 United Kingdom .

Primary Examiner—Max Hindenburg
Attorney, Agent, or Firm—Walter C. Farley

[57] ABSTRACT

A blood sampling device comprises a pointed cannula (3, 23) at each end, a pre-evacuated sample container (1, 21) with a self-sealing stopper (2, 22) which can be perforated, a self-sealing membrane (8,28) which can be perforated and a blood-viewing chamber (7, 27) the walls of which are surrounded by transparent material arranged in front of the stopper (2, 22) in the direction of perforation. The chamber (7, 27) is arranged on the stopper (2, 22) and is sealed off essentially from the sample container (1, 21) by said stopper (2, 22) and from the patient by the membrane (8, 28).

7 Claims, 3 Drawing Sheets

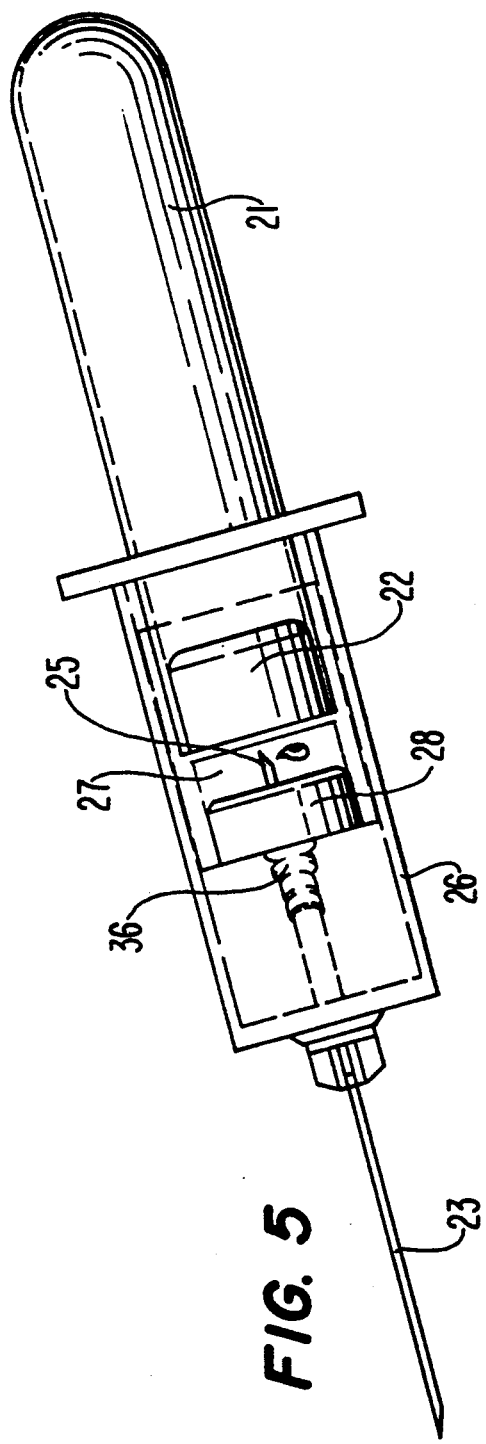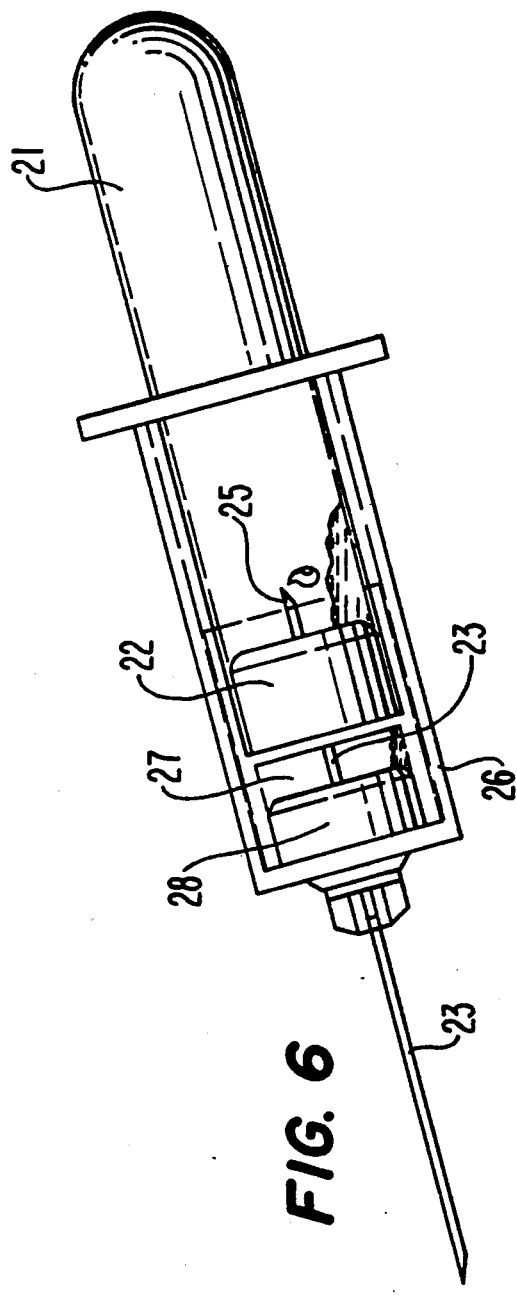

BLOOD SAMPLING DEVICE WITH BLOOD-VIEWING CHAMBER

FIELD OF THE INVENTION

This invention concerns a blood-taking device having an observation chamber and sealing devices to isolate the blood

BACKGROUND OF THE INVENTION

Blood-taking devices using vacuum suction have recently replaced the piston syringes that have been conventional for such purposes. However, the suction level cannot be fine-controlled when sucking the blood into an evacuated blood-sample container. Once the needle has pierced the stopper, suction is at full vacuum. While advantageous for other purposes, this condition is a drawback if the needle did not hit the vein but instead is located in the adjoining tissue. If this happens, the full vacuum produces a hematoma in the tissue which is disagreeable to the patient. Moreover, an evacuated blood-sample container was opened and vented without pulling in blood and must be replaced by a new one in the next attempt to puncture a vein.

Accordingly blood-taking devices of the above kind comprise a blood-observation chamber outside the blood-sample container and allowing to recognize the blood flowing out of the vein before vacuum is applied to the needle, i.e., before the needle has pierced the stopper. Because of the present higher sanitary requirements entailed by AIDS, hepatitis, etc., demanding total avoidance of patient blood which might contaminate the service personnel, it is necessary to design the blood-observation means as a chamber.

If necessary, such a blood-taking device allows hitting the tissue several times until the sought vein has been pierced. This is ascertained by blood entering the blood-observation chamber. Thereupon the needle is made to pierce the stopper.

A blood-taking device is known from the state of the art, namely from the German patent 28 35 101. In this known design, the blood-observation chamber is present at the middle of the needle. For that purpose the needle is made in two parts. Contrary to the known designs of other kinds, in this design the blood is sucked into the observation chamber. For that purpose the needle is pushed through the stopper into a suction chamber subjected to vacuum by means of a displaceable membrane, said suction chamber sucking the blood with a design-limited suction effect into the blood-observation chamber.

This known design suffers from the drawback that, on one hand, the manufacturing costs are high due to the complex needle construction. However, even when the physician operates the known blood-taking device, substantial drawbacks are incurred due to the blood-observation chamber being mounted on the needle. As a rule several blood-sample containers must be filled consecutively for the different blood tests. The needle is left in the patient's vein and the blood-sample containers are applied consecutively. However, when the blood-sample container is being changed, the blood remains stationary for some time in the blood-observation chamber and begins to clot.

This may lead to clogging, as a result of which the suction of the next applied blood-sample container no longer suffices to suck in blood. Moreover, the partly clotted blood from the blood-observation chamber may render ineffective the typically present anti-coagulant in the next applied blood-sample container, leading to spuriousness in test results.

In the light of the above, the above state of the art was not accepted in practice.

SUMMARY OF THE INVENTION

The object of the present invention therefore is to create a blood-taking device which averts coagulation problems while being of a simple design as regards the needle and which is more economical.

In the blood-taking device of the invention, the chamber is located at the stopper, not at the needle. As seen in the direction of piercing, this chamber precedes the stopper and during the piercing motion is pierced first. If the needle is located by its front end in a vein, blood can issue into the chamber and be recognized through the chamber's transparent walls. Thereupon the stopper can be pierced and blood can be removed. The needle is then withdrawn from the stopper and the membrane. Together with the blood which is then in contact with the stopper, the blood in the chamber is then disposed of. Because the needle lacks a chamber, the above-described coagulation problems are avoided in multiple blood sampling. Advantageously, the needle and any holder affixed to it may be left unchanged. To implement the present invention, merely a minor modification is required at the stopper, entailing no more than slight retrofitting costs.

The features of claim 2 are advantageous. The stoppers of the blood-sample containers as a rule are equipped with protective sleeves to prevent the lab worker from coming into contact with the bloody underside of the stopper when opening the blood-sample container. The protective sleeve consists as a rule of a material different from that of the stopper and therefore is more easily shaped to form the chamber and, in particular, it is more easily made of a transparent material, which would be quite difficult regarding the stopper itself on account of the required elasticity and the vacuum tightness.

The features of claim 3 are advantageous. As a rule commercial blood-sample containers comprise a holder at the needle which encloses in a tubular manner the stopper and the blood-sample container. In order to pierce the stopper, this stopper or the protective sleeve accompanying it is displaced inside the tubular holder. Stops may assure that such a position can be easily found and maintained accurately when piercing while the rear needle end is present in the chamber. The stops therefore assure that the needle shall be in the proper observation position.

The features of claim 4 are advantageous. Obviously the membrane must be liquid-impermeable in order to keep back the blood contained in the chamber. The membrane is air-permeable in order that there be constant pressure balance with the ambient. This step avoids excess pressure building up in the chamber which, for instance, might arise from manufacturing defects or from use at higher altitudes (such as in aircraft). Excess pressure in the chamber might prevent the blood from entering the chamber, i.e., it might prevent proper display.

The features of claim 5 are advantageous. Such a narrow vent aperture in the chamber wall assures effective pressure balancing of the chamber inside with the ambient atmosphere, whereby blood always can enter from the needle into the chamber. The aperture is so narrow that no blood can pass. This is assured by the surface tension of the blod relative to the hydrophobic wall material. As long as the pressures and forces arising in expert handling are not exceeded, the aperture blocks any blood from passing.

The features of claim 6 are advantageous. Depending on the angle of rotation between holder and stopper, this kind of stop can be moved into or out of its stop function. If there is a displacement into a specific angular position, for instance preset by graduations, then there shall be a stop function. Following rotation into another marked angular position, the inside projection and the longitudinal channel engage one another and further advance is possible in order to pierce the stopper.

The features of claim 7 are advantageous. In this manner the membrane is made thin and easily pierced in the radially inner zone that is to be pierced by the needle. This thin and elastic zone however is reinforced by an externally adjoining, thicker region of the membrane to such an extent that it also can be pierced by a dull needle without being substantially deflected.

The invention is schematically illustrated in the drawings.

FIG. 1 is an axial representation of a first, highly schematic embodiment of the invention, FIG. 2 is an exploded sectional view of a blood-sample container of a second embodiment, FIG. 3 is a perspective of the vacuum blood-taking device of the second embodiment of the invention, FIG. 4 is a perspective of the vacuum blood-taking device of a third embodiment of the invention, and FIGS. 5, 6 are side views of the embodiment of FIG. 3 in the two significant operational positions.

DESCRIPTION OF THE PREFERRED EMBODIMENTS

Figure 1:
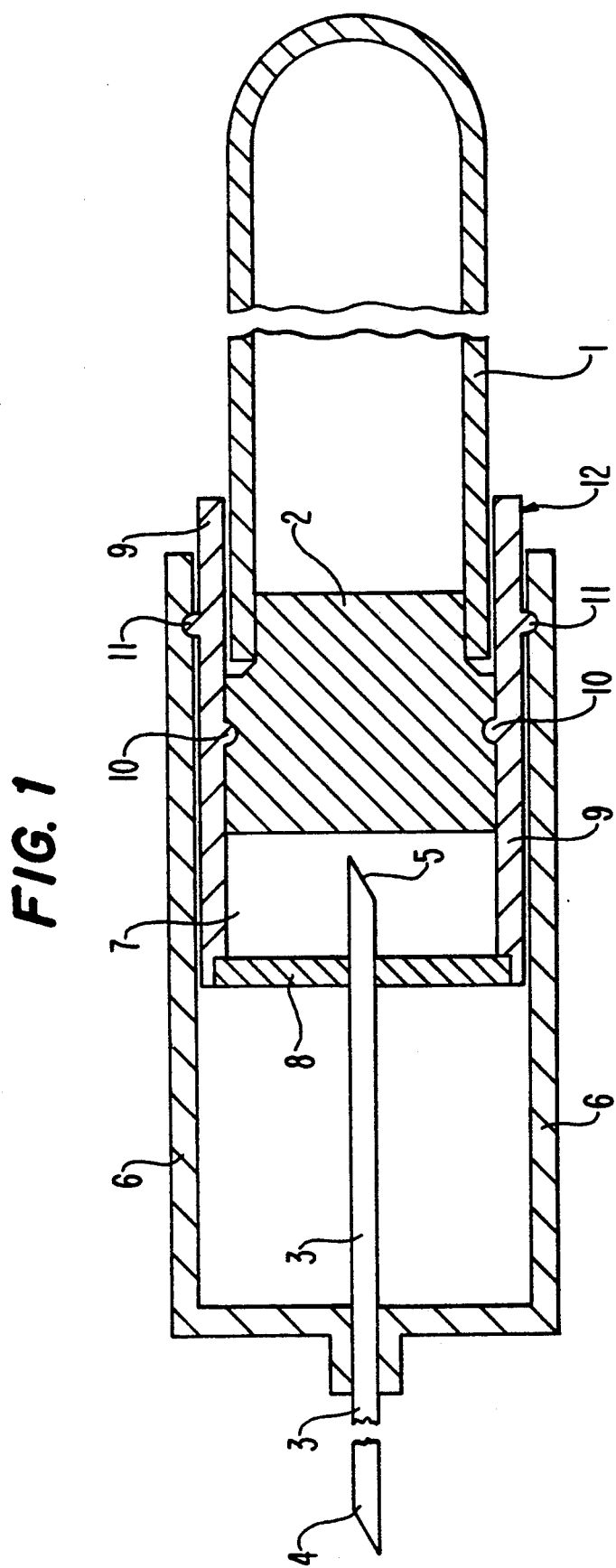

FIG. 1 shows a highly schematic embodiment of the invention.

Essentially the blood-taking device of the species being discussed here consists of a blood-sample or removal container 1, a stopper 2 and a needle 3.

As a rule and as shown in the drawing, the blood-sample container 1 assumes the conventional test-tube shape and consists of a suitably vacuum-tight and advantageously transparent material such as glass or plastic. The inside of the blood-sample container 1 is evacuated. The open end of the blood-sample container is sealed by a stopper 2 made of an elastic and suitably vacuum-tight material which moreover is self-sealing, that is, it will reseal a piercing duct made by the needle when the needle has been withdrawn, at least with respect to liquids.

The needle 3 tapers to a point at both ends, namely at the front end 4 facing the patient and also at the rear end 5 facing the stopper 2. The needle 3 is pushed by the front end 4 into a patient's vein. The rear end 5 is pushed through the stopper 2 into the inside of the blood-sample container 1. Thereupon the vacuum inside the blood-sample container 1 sucks the blood through the needle from the vein of the patient and fills the blood-sample container 1. Next the needle 3 is pulled out of the stopper 2 and the blood-sample container 1 sealed by the stopper 2 then can be moved into a lab where, following removal of the stopper 2, the blood can be tested.

As a rule, a holder 6 is provided at the needle 3 and is affixed by a transverse end wall and by a reinforced hub zone to the center part of the needle 3, the holder overlapping in tubular manner the stopper 2 and the blood-sample container 1. The holder 6 makes it easier to handle the needle when piercing the patient's vein and, because of its tubular guiding enclosure of the stopper 2, facilitates proper, centered piercing of the stopper 2 by the needle.

To know whether the pushed needle 3 has hit a vein in the patient, the rear end 5 of the needle must be observed. If blood is issuing there, a vein was hit. If no blood issues, the needle must be withdrawn a little and piercing must be renewed. This blood, which serves only as an indicator, shall not reach the ambient but must be retained in the blood-taking device. Therefore a chamber 7 must be provided allowing good observation of the blood which however shall remain enclosed.

In the invention, this chamber 7 is located on the side of the stopper 2 which is away from the blood-sample container. Seen in the direction of the needle 3, the chamber is bounded by the stopper 2 and by a membrane 8 and further by a transparent protective sleeve 12 consisting laterally of a cylindrical tube wall 9 and enclosing in sealing manner the stopper 2 membrane 8 being mounted at the inner end of sleeve 12. In this manner the chamber 7 is enclosed in sealing manner on all sides. From the side, the rear end 5 of the needle 3 and any blood issuing there can be observed through the tubular wall 9 when the needle is in the position shown in the Figure. If blood is noticed issuing, then this indicates that the needle by its front end 4 is in a vein. Thereupon the blood-sample container 1 can be moved farther toward the needle until the rear end 5 of this needle pierces the stopper 2.

In the embodiment shown, the tubular wall 9 not only connects the membrane 8 and the stopper 2, but also projects beyond the stopper as far as the neck zone of the blood-sample container 1. Accordingly in this case the tubular wall 9 serves as the conventional protective sleeve 12 present anyway which shall prevent the lab worker from touching with his fingers the bloody underside of the stopper when pulling out same in the lab.

In the embodiment shown, the stopper 2 is blocked by beads 10 on the inside of the tubular wall 9. Other suitable holding means for the stopper also may be provided.

The tubular wall 9 is provided at its outside with snap-in beads 11 which, in the longitudinal position shown, engage snap-in channels on the inside of the holder 6 and in this manner form a detent which, when the stopper 2 is advancing toward the needle 3, determines a position wherein the rear end 5 of the needle 3 is precisely located inside the chamber 7. By somewhat increasing the advance-force, the detent function can be overcome and the stopper 2 can be advanced farther.

In the embodiment shown, where a holder 6 tubularly enclosing the chamber 7 is present at the needle 3, the blood must be observed through two walls 6, 9. Care must therefore be taken that the wall materials be adequately transparent.

The material of the membrane 8 shall allow satisfactory piercing by the needle and also be self-sealing, in the same manner as the stopper 2, and as a rule therefore may be made of the same material. Attention must furthermore be paid when making the membrane that excess pressure be avoided in the chamber. This can be achieved by making the membrane especially flexible, for instance in the form of a bellows, or by making it from a water-impermeable but air-permeable material, whereby there always shall be the same pressure in the chamber as in the ambient. Moreover a tiny venting hole may be present in the tubular wall 9.

In a simplified embodiment, the chamber 7 also may be completely enclosed by the material of the stopper 2, i.e., it may be in the form of a cavity in the stopper; this would simplify the design but may entail material problems because of the required transparency.

In deviation from the above embodiment, the chamber 7 also may assume other geometries, for instance being a transparent, semi-spherical membrane bubble on the outside of the stopper 2. But as a rule it is more advantageous to make it as in the shown embodiment, with the tubular wall 9 being the sidewall of separate, clearly transparent material. Also there is the possibility to so design the chamber that it evinces a further partition relative to the stopper 2, whereby manufacturing advantages may be achieved.

FIGS. 2, 3, 5 and 6 show a preferred embodiment of the invention of which the basics are the same as in the simplified embodiment mode of FIG. 1. To the extent possible the same reference numerals are used, though each time raised by "20".

Figure 2:
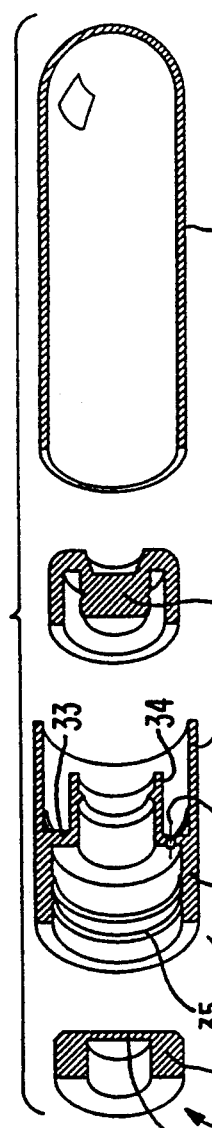

FIG. 2 shows that the blood-sample container 21 corresponds to the conventional basic shape. The protective sleeve 32 however has been substantially modified, being made particularly to meet the requirements of injection molding. Its tubular wall 29 comprises an inside flange 33 at the longitudinal center, this flange bearing a tube stub 34 pointing toward the blood-sample container 21 and receiving in conventional manner the stopper 22, itself conventional, which is plugged and held onto it in reliable manner.

Peripheral, inner ribs 35 are present on the tubular wall 29 on the side of the inner flange 33 that is away from the blood-sample container 21. Ribs 35 hold the membrane 28 which is inserted flush and like a stopper into the end of the tubular wall 29 to come to rest against the inner ribs 35 which act as limit stops.

The membrane 28 comprises a radially inside zone 38 with a relative thin wall and a radially outer zone 39 with a relatively thicker wall. As a result, the inner thinner zone 38 is easily pierced by the needle 3 on one hand, but on the other it is so well strengthened by the thicker outer zone 39 that it will yield only slightly when under pressure from the piercing needle 3 so that such piercing is reliably and rapidly assured.

To balance the pressure inside the chamber 27, the membrane 28 may be made of a gas-permeable material. Preferably, however, venting is used in the form of a borehole 37 passing from the chamber 27 through the inner flange 33. The material traversed by the borehole 37 must be hydrophobic. With a given surface tension of the blood and with given maximum forces pushing the blood through the borehole as may arise from pressure differentials and accelerations and which are not exceeded in professional treatment, blood cannot pass through the borehole below a certain borehole diameter for a particular surface tension.

Accordingly, the borehole 37 sets up communication between the chamber 27 and the annular region between the tubular wall 29 and the tube stub 34 receiving the stopper 22. Depending on the design of the stopper 22, it may occur that when said stopper is put in place, it will be forced by an end face against the inner flange 33 and thereby shall seal the borehole 37. In that case the due venting of chamber 27 would be prevented.

To prevent such an occurrence, advantageously the inner flange 33 shall be somewhat thinner, by means of a recess, on the side facing the stopper 22, in the region around the borehole 37, as shown by the section of the inner flange 33 of FIG. 2. Therefore, the stopper 22 cannot come to rest on the aperture of the borehole 37 in the vicinity of latter. Accordingly venting will always be preserved.

Figure 3:
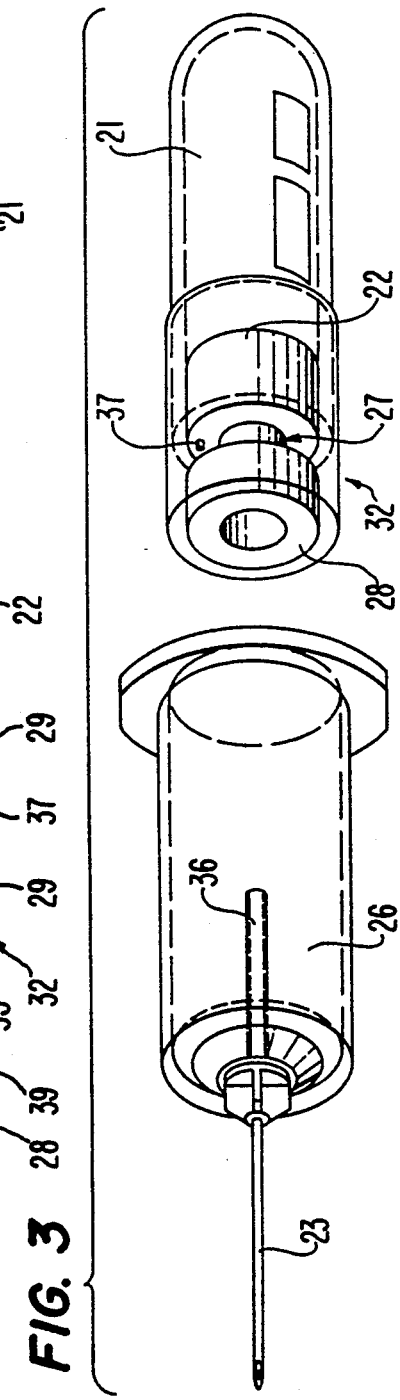

FIG. 3 is a perspective of the blood-sample container 21 together with the fully mounted, assembled protective sleeve 32 affixed on the blood-sample container. Also shown are the membrane 28 with its characteristic shape shown in FIG. 2, the stopper 22 in the tube wall 29 and also the borehole 37. This Figure shows that the protective sleeve with the tube wall 29 is made of a transparent material allowing viewing the inside of the chamber 27.

FIG. 3 moreover shows a holder 26 with a needle 23 and essentially corresponding to that of FIG. 1. The inner part of the needle 23 cannot be seen because it is covered by the conventional, closed rubber sheath 36 which is also pierced when the rear end of the needle 23 pierces the membrane 28 or the stopper 22 and which, after the needle has been withdrawn, resumes its initial shape and seals the needle with respect to the blood.

FIG. 5 shows the embodiment of FIG. 3 in side view, the fully mounted blood-sample container 21 equipped with stopper 22 having been pierced so far by the needle 23 that the needle's rear end 25 has fully entered the chamber 27. An issuing blood drop is shown. Again it is clearly shown how the rubber sheath 36 bunches together on the needle 23 when the needle pierces membrane 28.

FIG. 6 shows the system of FIG. 5 in the operational position, wherein the blood-sample container 21 has been moved as far as the stop on the needle 23, so that the rear needle end 25 now is located inside the blood-sample container 21 whereby the blood therein, as shown, can be sucked by the vacuum.

Comparison of FIGS. 5 and 6 shows that essentially two advance positions of the blood-sample container 21 are required relative to the needle 23 or the holder 26, the advance position of FIG. 6 being automatically implemented by the natural stop at the base of the holder 26, whereas the position of FIG. 5 however must be set by the physician using his fingertip sense of touch and by his observation.

This process can be facilitated by the stop means 11 of the embodiment of FIG.1. Said stop means however incurs the drawback it may be cumbersome at times and the application of force may lead to jitter and hence to pain in the patient.

Figure 4:
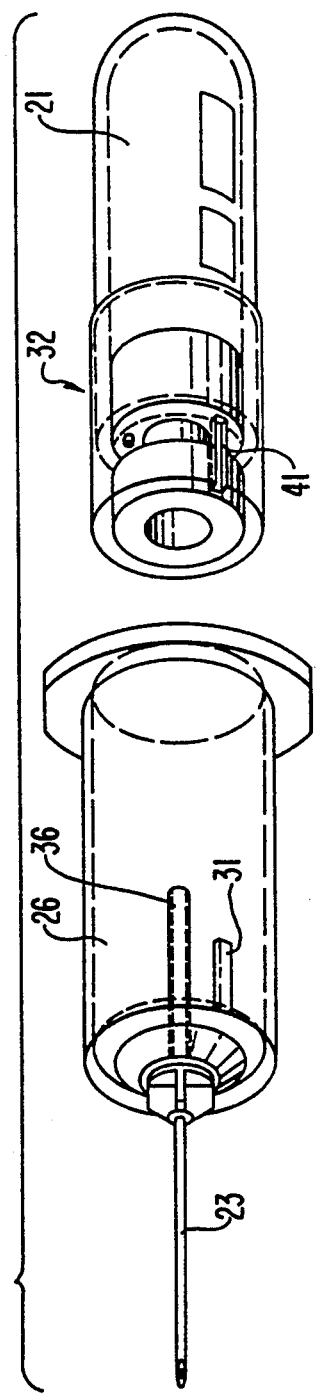

As regards the embodiment of FIG. 4, which matches the design of FIG. 3 in the other parts, an axially extending inside tang 31 is provided which projects radially inward from the inside of the cylinder wall of the holder 26. A longitudinal channel 41 starting at the outside is present in the tube wall 29 of the protective sleeve 32 and can receive the inner tang 31 if the relative angular positions of the parts shown in FIG. 4 is proper. Thereupon the blood-sample container 21 can be advanced as far as the base of the holder 26, that is until the operational position of FIG. 6 has been reached. If on the other hand the two parts shown in FIG. 4 are mutually rotationally apart, then the advance only can take place as far as the stop of the end face of the tube wall 29, against the inner tang 31: this is the position of FIG. 5. In this embodiment therefore the advance may be very easily achieved manually and, upon rotation, the advance may proceed in gentle manner.

In case the inner diameters of the blood-sample container 21 and of the protective sleeve 32 are very small compared with the inside diameter of the holder 26, flange-like broadening means may be provided on the outside of the tube wall 29 for guidance in the holder 26. The channel 41 then may be present in said means.

The sectionally shown protective sleeve 32 of FIG. 2 is optimized for injection molding. As the expert understands at once, it may be injected into one mold consisting of two axially assembled cores. This is also the case for the arrangement of the axial borehole 37 which therefore can be removed from the mold in the core ejection direction.

Again the structure of the stop means shown in the embodiment of FIG. 4 is optimized for injection molding. Channel 41 is arranged longitudinally so that the channel can be removed in the ejection direction of the cores, that is axially, whereby the mold may be simple and economical. This also applies to the inside tang 31 at the holder 26 which is mounted axially and therefore assures in similar manner easy ejection and simple mold-shape.

I claim:

1. A blood sampling device comprising the combination of
   a hollow needle pointed at both ends;
   means for supporting said needle with a first end thereof positioned to enter a blood vessel of a patient;
   a single pre-evacuated blood sample chamber having a central axis, said sample chamber slidable engaging said means for supporting said needle;
   a single self-sealing stopper which can be pierced by said needle, said stopper being mounted at one end of said sample chamber; and
   a blood observation chamber positioned axially toward said needle from said sample chamber, said observation chamber being closed at one end by said stopper and having a transparent side and a needle-piercable membrane closing an end away from said stopper, said observation chamber having an internal pressure substantially equal to ambient pressure;
   said sample chamber and said observation being joined into a fixedly connected working unit substantially inseparable during the process of taking a blood sample and being separable for removing the blood sample.

2. A device according to claim 1 wherein said means for supporting said needle includes a generally tubular holder attached to a central part of said needle, said holder enclosing said stopper and being axially movable relative to said stopper during a blood taking process, said device further comprising stop means for limiting axial motion of said holder relative to said stopper when said needle has pierced said membrane.

3. A blood sampling device comprising the combination of
   a hollow needle pointed at both ends;
   means for supporting said needle with a first end thereof positioned to enter a blood vessel of a patient;
   a single pre-evacuated blood sample chamber having a central axis, said sample chamber being slidably coupled to said means for supporting said needle;
   a single self-sealing stopper which can be pierced by said needle at one end of said sample chamber; and
   a blood observation chamber comprising a transparent protective tubular sleeve overlapping said one end of said sample chamber and attached to said stopper, said observation chamber projecting beyond said stopper and being closed at one end by said stopper and having a needle-piercable membrane closing an end away from said stopper and toward said first end of said needle, said observation chamber having an internal pressure substantially equal to ambient pressure;
   said sample chamber and said observation chamber being joined into a fixedly connected working unit substantially inseparable during the process of taking blood sample and being separable for removing the blood sample.

4. A device according to claim 3 wherein said observation chamber includes a bidirectional vent aperture consisting of a borehole in a wall made of a hydrophobic material, said borehole having a diameter so small that said vent aperture will not pass blood in the presence of the pressures and forces arising in expert handling of said device.

5. A device according to claim 3 wherein said means for supporting said needle includes a generally tubular holder attached to a central part of said needle, said holder enclosing said sleeve and being axially movable relative to said sleeve during a blood taking process, said device further comprising stop means for limiting axial motion of said holder relative to said sleeve when said needle has pierced said membrane.

6. A device according to claim 5 wherein said stop means comprises an axially extending rib on an inner surface of said holder at the end thereof closes to said needle and an axially extending channel on an outer surface of said sleeve.

7. A device according to claim 6 wherein said membrane includes a tubular wall and a transverse radially extending inner portion of smaller wall thickness than said tubular wall.

* * * * *